United States Patent [19]

Boomgaarden et al.

[11] Patent Number: 4,991,189
[45] Date of Patent: Feb. 5, 1991

[54] COLLIMATION APPARATUS FOR X-RAY BEAM CORRECTION

[75] Inventors: Jonathan C. Boomgaarden, Waukesha; Thomas L. Toth, Brookfield; August O. Englert, Waukesha, all of Wis.

[73] Assignee: General Electric Company, Milwaukee, Wis.

[21] Appl. No.: 509,598

[22] Filed: Apr. 16, 1990

[51] Int. Cl.$^5$ ............................................. G01N 23/00
[52] U.S. Cl. ......................................... 378/4; 378/151
[58] Field of Search ............................ 378/151, 4, 150

[56] References Cited

U.S. PATENT DOCUMENTS

4,559,639  12/1985  Glover et al. .......................... 378/19

Primary Examiner—Craig E. Church
Attorney, Agent, or Firm—Quarles & Brady

[57] ABSTRACT

A computed tomography system corrects image errors resulting from misalignment of the fan beam as a result of placement of the x-ray tube, thermal drift of the x-ray tube anode of mechanical stresses of the gantry or x-ray tube. Misalignment is determined alternately by means of a z-axis offset detector which detects movement of the exposure area of the CT fan beam or a predictive model that calculates thermal drift of mechanical deflection of the focal spot of the x-ray tube based on previous use. The system includes a collimator with a controllable z-axis position which may be controlled to reduce z-axis offset of the fan beam exposure area or to make the fan beam more parallel with the imaging plane of the CT system.

9 Claims, 5 Drawing Sheets

COLLIMATION APPARATUS FOR X-RAY BEAM CORRECTION

BACKGROUND OF THE INVENTION

This invention relates to x-ray collimators for use in computed tomography systems and the like and specifically to a collimation system for correcting errors in the x-ray fan beam location and angle of incidence with the detector mechanism resulting from misalignment of the position of the x-ray tube focal spot.

Computed tomography systems, as are known in the art, typically include an x-ray source collimated to form a fan beam directed through an object to be imaged and received by an x-ray detector array. The x-ray source and detector array are orientated to lie within the x-y plane of a Cartesian coordinate system, termed the "imaging plane". The x-ray source and detector array may be rotated together on a gantry within the imaging plane, around the image object, and hence around the z-axis of the Cartesian coordinate system. Rotation of the gantry changes the angle at which the fan beam intersects the imaged object, termed the "gantry" angle.

The detector array is comprised of detector elements each of which measures the intensity of transmitted radiation along a ray path projected from the x-ray source to that particular detector element. At each gantry angle a projection is acquired comprised of intensity signals from each of the detector elements. The gantry is then rotated to a new gantry angle and the process is repeated to collect an number of projections along a number of gantry angles to form a tomographic projection set.

Each acquired tomographic projection set may be stored in numerical form for later computer processing to reconstruct a cross sectional image according to algorithms known in the art. The reconstructed image may be displayed on a conventional CRT tube or may be converted to a film record by means of a computer controlled camera.

The x-ray source is ordinarily an x-ray "tube" comprised of an evacuated glass x-ray envelope containing an anode and a cathode. X-rays are produced when electrons from the cathode are accelerated against a focal spot on the anode by means of a high voltage across the anode and cathode. The voltage applied across the anode and cathode, the current flowing between the anode and cathode, and the duration of the exposure, for a given x-ray procedure, is termed the "exposure technique".

The efficiency of energy conversion in generating x-rays is low, and as a consequence, considerable heat is developed in the anode of the x-ray tube. For this reason, the anode may be rotated at high speeds so that the focal spot constantly strikes a new and cooler area of the anode. Even so, the surface temperature of the anode may rise as high as 2000° C. during the acquisition of the projections for a series of tomographic projection sets and the anode supporting structure including the shaft on which it rotates may rise to 400° C. or more.

As the x-ray source heats up, thermal expansion of the anode supporting structure results in movement of the focal spot relative to the glass envelope of the x-ray tube and movement of the fan beam. The focal spot may move as much as 0.25 mm (0.01 inch) due to thermal expansion during the acquisition of a series of tomographic projections.

The anode shaft is aligned with the z-axis, about which the gantry rotates, to prevent gyroscopic torques from acting on the rotating anode during movement of the gantry. Thermal expansion of the anode support structure therefore tends to move the focal spot along the z-axis. With a fixed collimator position, movement of the focal spot in the z-axis sweeps the fan beam in the opposite direction along the surface of the detector array.

Another source of motion of the focal spot is mechanical stress of the gantry and rotating anode as the gantry rotates. This stress results from the changing angle of gravitational acceleration and the changing magnitude of centripetal acceleration as a function of the rotational velocity of the gantry, acting on the gantry and anode. These resulting forces contribute up to 0.25 mm (0.01 inch) of additional focal spot motion.

The detector array may be an ionization type detector or solid state detector as are known in the art. Both detector types exhibit changes in their sensitivity to x-rays as a function of the position of the fan beam along their surface. Accordingly, movement of the fan beam as a result of thermal drift or mechanical deflection of the x-ray source focal spot may change the strength of the signal from the detector array. Such changes in signal strength during the acquisition of a tomographic projection set produce ring like image artifacts in the resultant reconstructed image.

With a fixed collimator position, movement of the focal spot in the z-axis also affects the alignment of the fan beam with the imaging plane. The mathematics of image reconstruction assumes that each acquired projection is taken within a single plane. Lack of parallelism of the fan beam with the imaging plane will also produces shading and streak image artifacts in the reconstructed image. Also, for small slice widths, the misalignment due to motion induced stress on the gantry and anode may significantly enlarge the effective slice width of images reconstructed from opposing but misaligned views. This motion induced misalignment will reduce contrast resolution for small imaged objects, such as lesions, making them harder to detect. In addition, the spatial resolution of the CT imaging system will be reduced for high frequency features at oblique angles to the slice.

SUMMARY OF THE INVENTION

According to the present invention the collimator position $C_z$ is automatically adjusted so as to control the alignment of the fan beam plane and therefore to reduce image artifacts. A z-axis offset detector, positioned to intercept the fan beam, produces a fan beam position signal dependant on the position of the fan beam plane and an error signal is generated from that position signal. A collimator controller responsive to the error signal, changes the collimator position $C_z$ so as to reduce the error signal.

It is one object of the invention to reduce image artifacts resulting from the changes in the fan beam position with respect to the detector. In a first embodiment, the error signal is made proportional the difference between the fan beam position and an alignment point. The collimator controller repositions the collimator to reduce the error signal thereby aligning the fan beam plane with the alignment point. Drift of the fan beam plane with respect to the detector array is thereby corrected.

It is another object of the invention to reduce image artifacts resulting from the deviation of the angle of the fan beam plane from the angle of the image plane. In a second embodiment, the error signal is made proportional to the difference between the position of the fan beam and the position of the collimator. The collimator controller repositions the collimator to reduce the error signal by making the collimator position equal to the position of fan beam, which aligns the fan beam plane with the imaging plane. Deviation of the angle of the fan beam plane from the image plane is thereby corrected.

It is another object of the invention to permit the rapid alignment of the x-ray source with the detector array during initial assembly or later replacement of the x-ray source or detector array. The adjustable collimator of the present invention permits the x-ray source to be aligned approximately by mechanical stops. Final, accurate alignment is performed automatically by movement of the collimator.

It is yet another object of the invention to allow the use of solid state detector array elements with higher variations in sensitivities as a function of the position of the fan beam on their surface (z-axis sensitivity). Presently, solid state detector elements are culled to select units with low z-axis sensitivity. The present invention, by reducing the z-axis drift of the fan beam, permits the use of detector elements with higher z-axis sensitivities, thereby reducing waste and expense.

During the initial projection acquisitions, the correct collimator position is estimated based on the previous use of the x-ray tube and hence the heat absorbed by the x-ray tube anode and its supporting structure. A memory stores the previous exposure techniques used with the x-ray tube and the time of use of each technique. From this information, the thermal expansion of the tube is predicted and a value of the current focal spot position $F_z$ estimated. The collimator controller positions the collimator in response to the predicted value of $F_z$.

It is thus another object of the invention to allow for correction of the fan beam plane prior to the determination of fan beam position by means of the z-axis offset detector.

In another embodiment, mechanical stresses acting on the gantry and the x-ray tube are estimated based on the gantry speed and angle. From this information, the mechanical deflection of the focal spot is estimated and a value of the current focal spot position $F_z$ computed. The collimator controller positions the collimator in response to the predicted value of $F_z$.

It is thus another object of the invention to allow for correction of the fan beam plane resulting from motion induced mechanical stresses.

Other objects and advantages besides those discussed above shall be apparent, to those experienced in the art, from the description of a preferred embodiment of the invention which follows. In the description, reference is made to the accompanying drawings, which form a part hereof, and which illustrate one example of the invention. Such example, however, is not exhaustive of the various alternative forms of the invention, and therefore reference is made to the claims which follow the description for determining the scope of the invention.

BRIEF DESCRIPTION OF THE DRAWINGS

FIG. 3 is a perspective view of the collimator assembly of the present invention;

FIG. 4 (a) and (b) are cross sectional views of the mandrel of the collimator of FIG. 3 showing orientation of the mandrel for thick and thin fan beams respectively;

DETAILED DESCRIPTION OF THE PREFERRED EMBODIMENT

Figure 1:
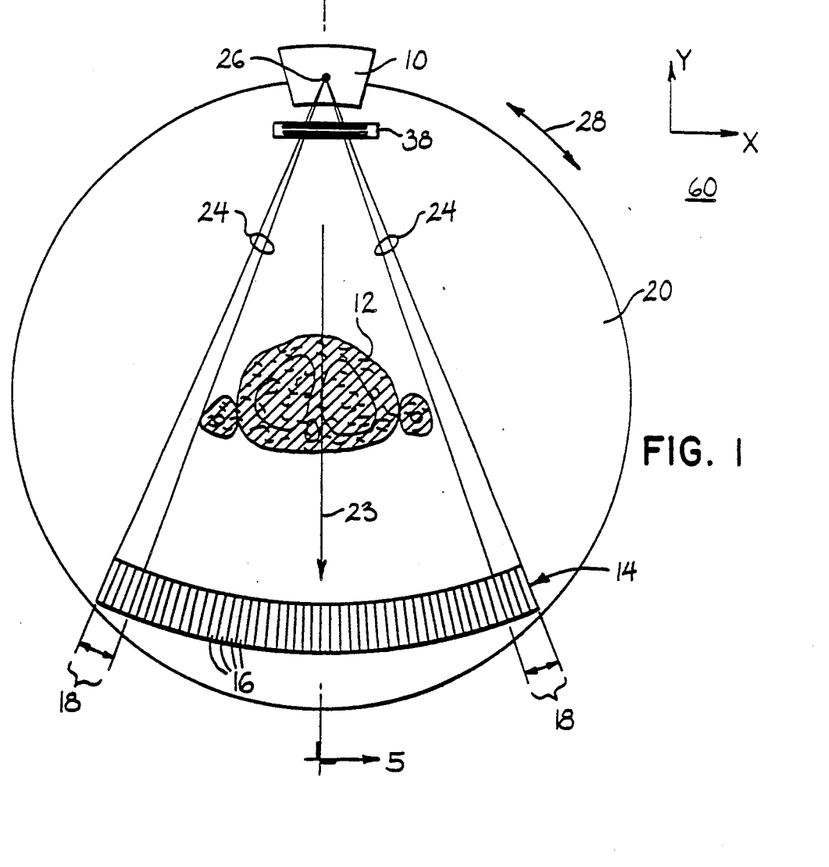
FIG. 1 is a schematic representation of an x-ray source and x-ray detector as may be used with the present invention.

Referring to FIG. 1, a gantry 20, representative of a "third generation" computed tomography scanner, includes an x-ray source 10 collimated by collimator 38 to project a fan beam of x-rays 22 through imaged object 12 to detector array 14. The x-ray source 10 and detector array 14 rotate on the gantry 20 as indicated by arrow 28, within an imaging plane 60, aligned with the x-y plane of a Cartesian coordinate system, and about the z-axis of that coordinate system.

The detector array 14 is comprised of a number of detector elements 16, organized within the imaging plane 60, which together detect the projected image produced by the attenuated transmission of x-rays through the imaged object 12.

The fan beam 22 emanates from a focal spot 26 in the x-ray source 10 and is directed along a fan beam axis 23 centered within the fan beam 22. The fan beam angle, measured along the broad face of the fan beam, is larger than the angle subtended by the imaged object 12 so that two peripheral beams 24 of the fan beam 22 are transmitted pas the body without substantial attenuation. These peripheral beams 24 are received by peripheral detector elements 18 within the detector array 14.

Figures 3, 4A, 4B:
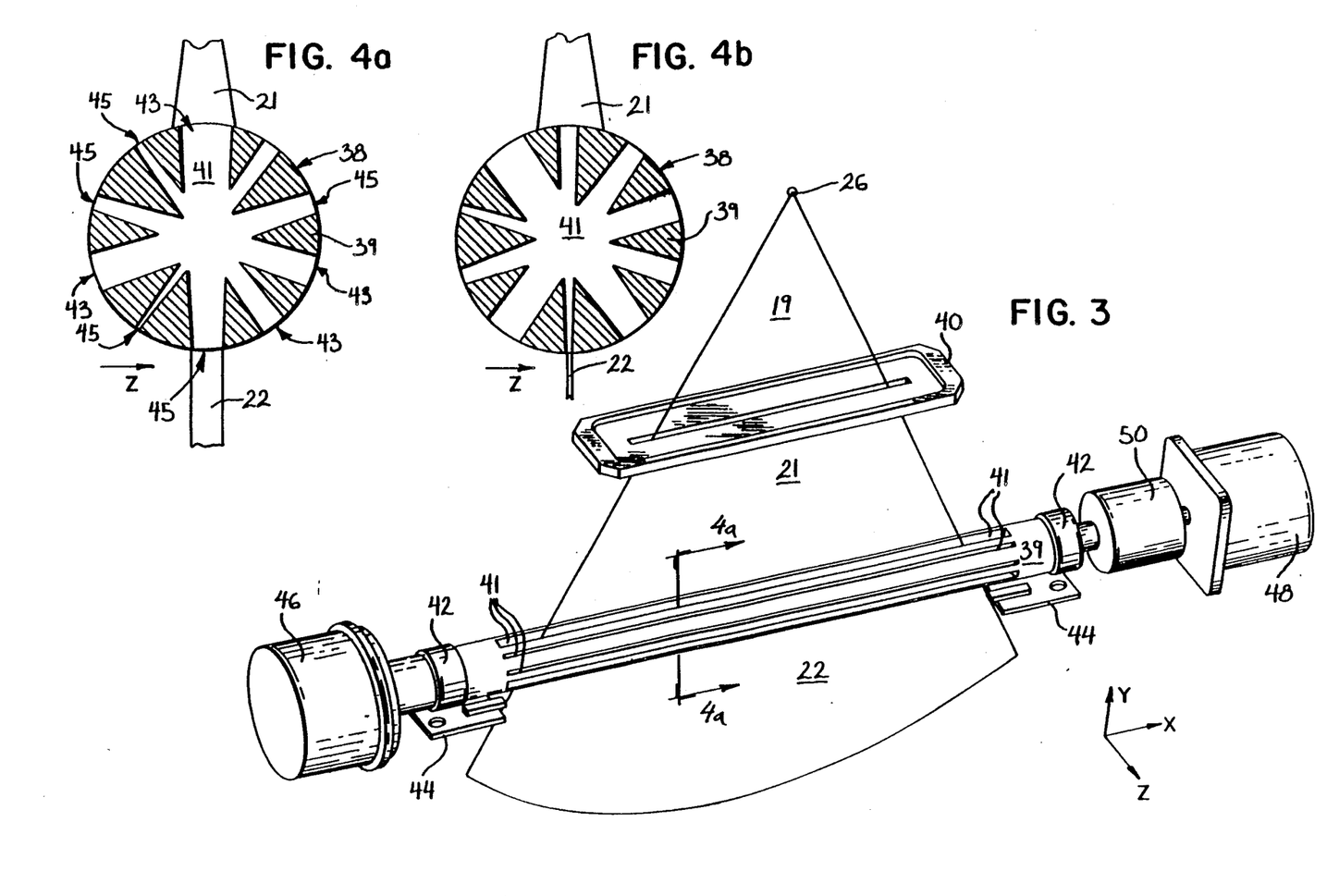

Referring to FIG. 3, uncollimated x-rays 19 radiating from the focal spot 26 in the x-ray source 10 (not shown in FIG. 3) are formed into a coarse fan beam 21 by primary aperture 40. The coarse fan beam 21 is collimated into fan beam 22 by means of collimator 38.

Referring generally to FIGS. 3, 4(a) and 4(b), collimator 38 is comprised of a cylindrical x-ray absorbing molybdenum mandrel 39 held within the coarse fan beam 21 on bearings 42 allowing the mandrel 39 to rotate along its axis. A plurality of tapered slots 41 are cut through the mandrel's diameter and extend along the length of the mandrel 39. The slots 41 are cut at varying angles about the mandrel's axis to permit rotation of the mandrel 39 to bring one such slot 41 into alignment with the coarse fan beam 21 so as to permit the passage of some rays of the coarse fan beam 21 through the slot 41 to form fan beam 22.

Referring to FIG. 4(a) and 4(b), the tapered slots 41 are of varying width and hence the rotation of the mandrel 39 allows the width of the fan beam 22 to be varied between a narrow (1 mm) as shown in FIG. 4(b) and wide (10 mm) as shown in FIG. 4(b). The slots 41 ensure dimensional accuracy and repeatability of the fan beam 22.

The slots 41 are tapered so that the entrance aperture 43 of each slot 41, when orientated with respect to the coarse fan beam 21, is wider than the exit aperture 45. The exit aperture 45 defines the width of the fan beam 22 and the extra width of the entrance aperture 43 prevents either edge of the entrance aperture 43 from blocking the coarse fan beam 21 during rotation of the mandrel 39 when such rotation is used to control the alignment of the fan beam axis 23 as will be discussed in detail below.

Referring again to FIG. 3, a positioning motor 48 is connected to one end of the mandrel 39 by flexible coupling 50. The other end of the mandrel 39 is attached to a position encoder 46 which allows accurate positioning of the mandrel by motor 48. Fan beam angle shutters 44 at either ends of the mandrel 39 control the fan beam angle.

Figure 5:
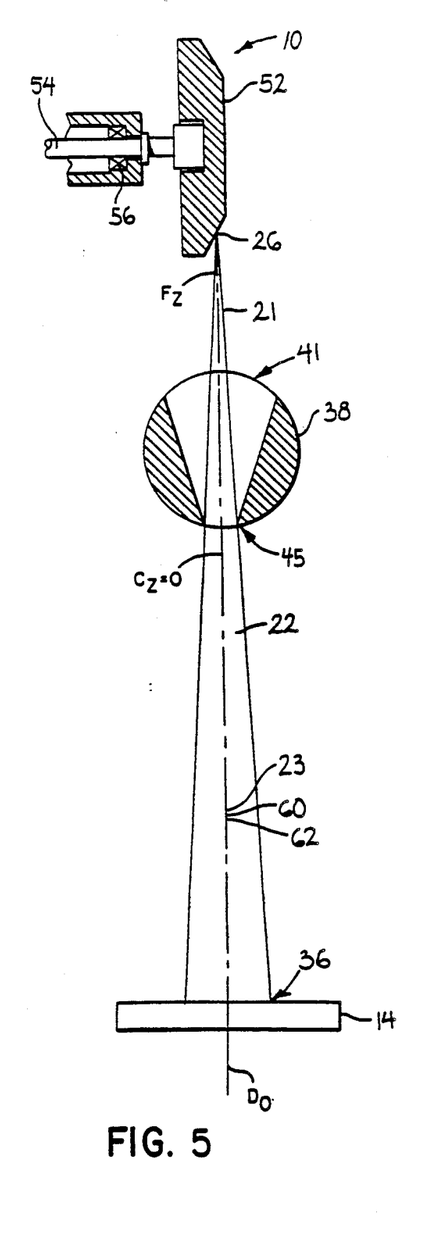
FIG. 5 is a simplified cross sectional view of the path of the x-ray fan beam, taken along line 5—5 in FIG. 1, with the x-ray tube anode, the collimator and the detector array exaggerated for clarity.

Referring to FIG. 5, the x-ray source 10 is comprised of a rotating anode 52 held within an evacuated glass tube (not shown) and supported by supporting structure including principally anode shaft 54 which is held on bearings 56 (one shown). The coarse fan beam 21 emanates from focal spot 26 at the surface of the anode 52. The position of the focal spot 26 along the z-axis will be termed $F_z$ and will be defined as being equal to zero when the focal spot 26 is at a reference point $F_0$ defined further below.

The coarse fan beam 21 is then collimated by the collimator 38 to form a fan beam 22 as previously described. The z-axis position of the center of the exit aperture 45, for the slot 41 that is aligned with the coarse fan beam 21 (shown in FIG. 3) will be termed $C_z$ and will be defined as being equal to zero when the center of the exit aperture 45 is at a reference line $C_O$ which will also be defined below.

Figure 2:
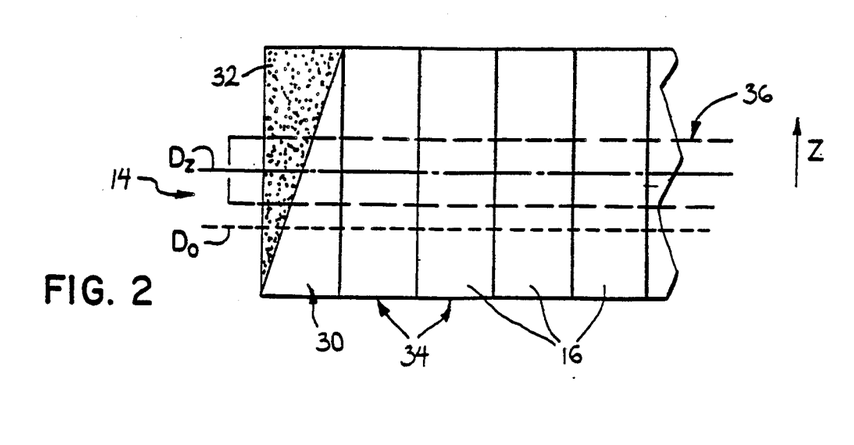
FIG. 2 is a schematic view of the peripheral detector elements of the detector array of FIG. 1.

Referring to FIG. 2, the fan beam 22 (not shown in FIG. 2) exposes an area 36 on the face of the detector array 14 and accordingly on the face of the peripheral detector elements 18. Peripheral detector elements 18 include reference detectors 34 and a z-axis offset detector 30. The face of z-axis offset detector 30 is partially occluded by a wedge filter 32 which is tapered to block a changing percentage of the fan beam 22 as a function of the fan beam position with respect to the z-axis offset detector 30. The z-axis position of the center of exposure area 36 with respect to the detector array 14 will be termed the fan beam position, $D_z$ and is defined as equal to zero when $D_z$ is equal to a reference value D0 as will be defined below. A detailed description of the detection of fan beam position, through the use of a wedge filter 32 in conjunction with a z-axis offset detector 30 and reference detector 32 is described in U.S. Pat. No. 4,559,639, entitled: "X-ray Detector with Compensation for Height-Dependant Sensitivity and Method of Using Same", issued on Dec. 17, 1985, assigned to the same assignee as the present invention, and hereby incorporated by reference.

$F_O$, $C_O$, and $D_O$ are defined such that the fan beam axis 23 is parallel to the imaging plane when the focal spot is at $F_O$ and the collimator is at $C_O$ and the fan beam is centered at $D_O$ on the detector array 14.

Referring again to FIG. 5, the plane containing the centerline of the focal spot 26, the center line of the exit aperture 45, and the centerline of the exposure area 36, and thus bisecting the fan beam 22 in the z axis direction, will be termed the "fan beam plane" 62.

Figure 6:
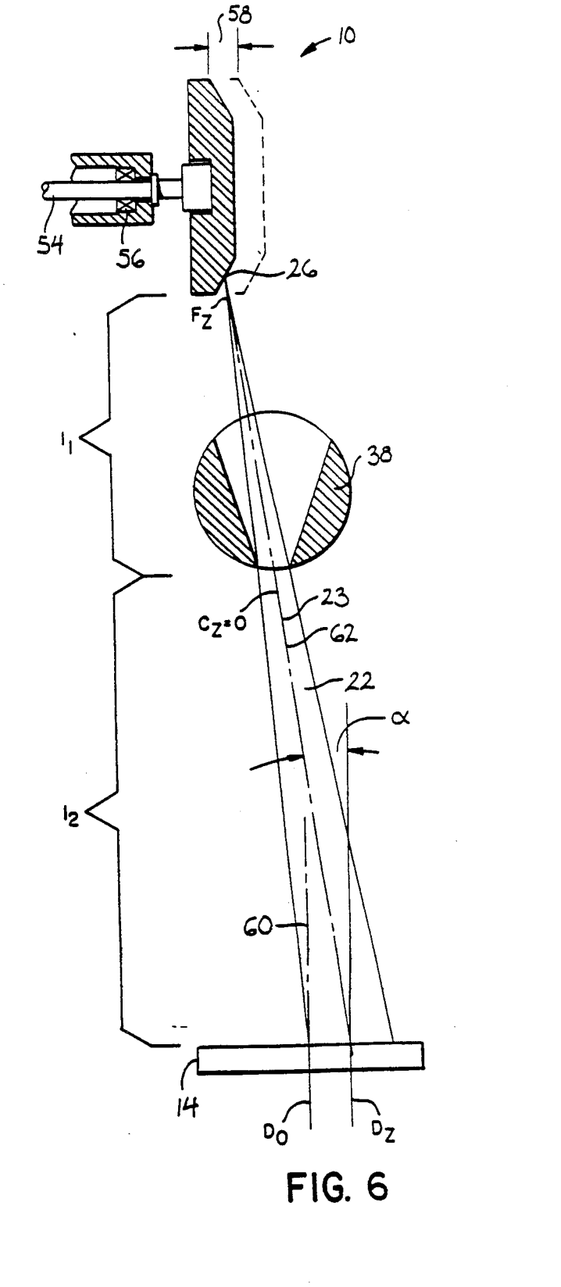
FIG. 6 is a cross sectional view, similar to that of FIG. 5, showing the effect of thermal drift of the x-ray anode on fan beam alignment.

As previously described, the focal spot 26 may not be aligned with the imaging plane 60 either because of thermal drift of the anode 52 and its supporting structure or because of minor misalignment of the x-ray source 10 during assembly. Referring to FIG. 6, the anode 52 is shown displaced from the imaging plane 60 by misalignment distance 58. The effect of this misalignment is to displace focal spot position $F_z$ away from the imaging plane 60 and to move the center of the fan beam exposure area 36 in the opposite direction according to the formula:

$$D_z = -F_z \cdot \frac{l_2}{l_1} \tag{1}$$

where $l_1$ is the distance between the focal spot 26 and the center of the exit aperture 45, and $l_2$ is the distance between the center of the exit aperture 45 and the detector array 14. For a typical computed tomography system the ratio $l_2/l_1$ is approximately 3.3.

As a result of the movement of the focal spot 26, as shown in FIG. 6, the exposure area 36 is no longer centered at $D_O$ and the fan beam plane 62 is no longer parallel with the imaging axis 60 but deviates by angle α.

Figure 7:
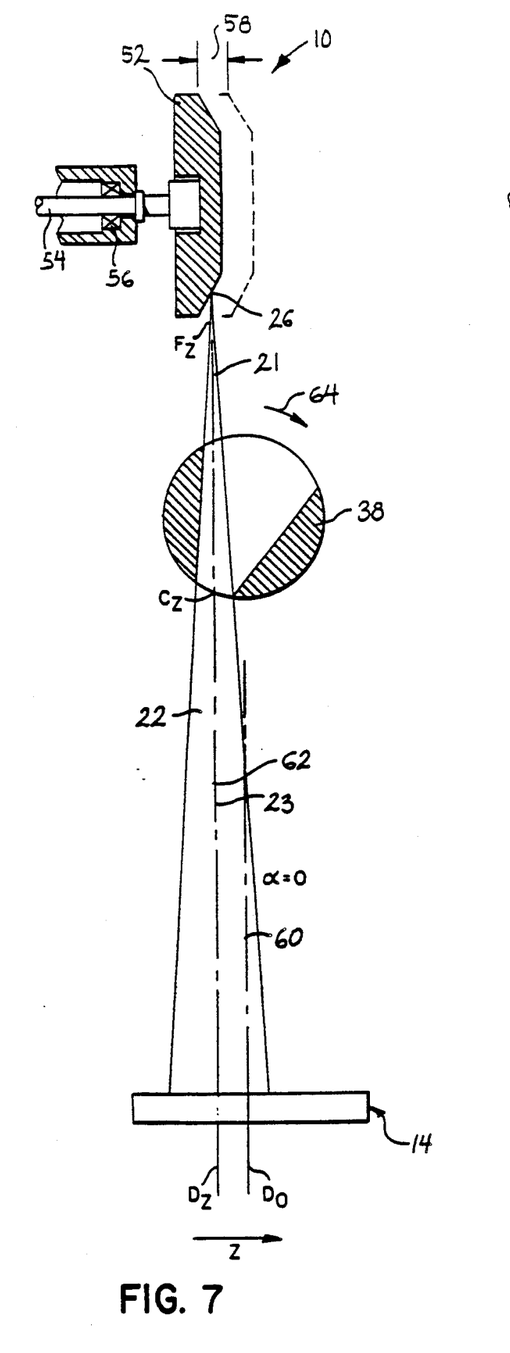
FIG. 7 is a cross sectional view, similar to that of FIG. 6, showing rotation of the collimator to make the fan beam plane parallel with the imaging plane.

Referring to FIG. 7, the collimator 38 may be rotated to position $C_z$ removed from the imaging plane 60. When $C_z$ is equal to $F_z$, then $D_z$ will also equal $C_z$ and the fan beam plane 62 will be restored to being parallel with the imaging plane 60. This correction of the angle of the fan beam plane 62 will be termed "parallelism correction".

Figure 8:
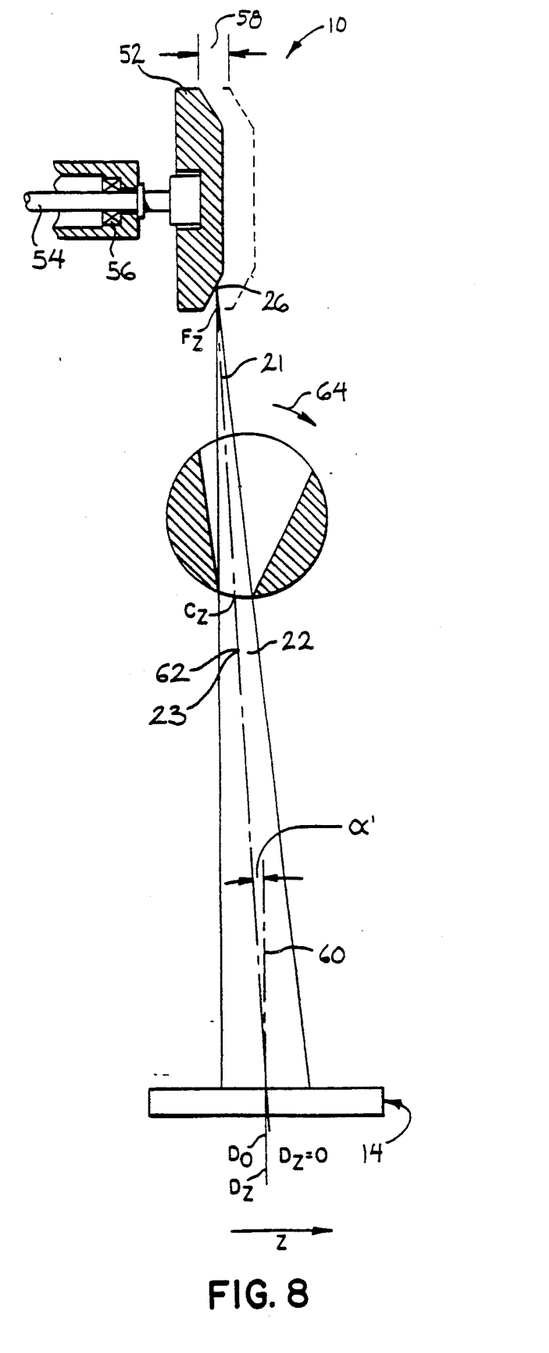
FIG. 8 is a cross sectional view, similar to that of FIG. 6, showing rotation of the collimator to align the fan beam within the detector array.

Alternatively, referring to FIG. 8, the collimator 38 may be rotated so that $C_z$ is equal to $$F_z \cdot \frac{l_2}{l_1 + l_2} .$$

$D_z$ will thus be made equal to $D_O$ and the exposure area 36 will again be centered at $D_O$. Correction of the position of the of the fan beam exposure area 36 with respect to the detector 14 will be termed "z-axis offset correction".

In summary, rotation of the collimator 38 may correct for misalignment of the fan beam plane 62 either to make it parallel with the imaging plane 60 or to bring the exposure area 36 into alignment with $D_O$ on the detector array 14. As previously discussed, both of these corrections will reduce image artifacts.

It will be understood by one skilled in the art that first a parallelism correction may be performed to make the fan beam plane 62 parallel to the imaging plane 60. The resulting $D_z$ value may then be defined as $D_O$ and maintained against thermal drift of the focal spot 26, to ensure constant detector 14 gain by means of continuing z-axis offset correction.

Figure 9:
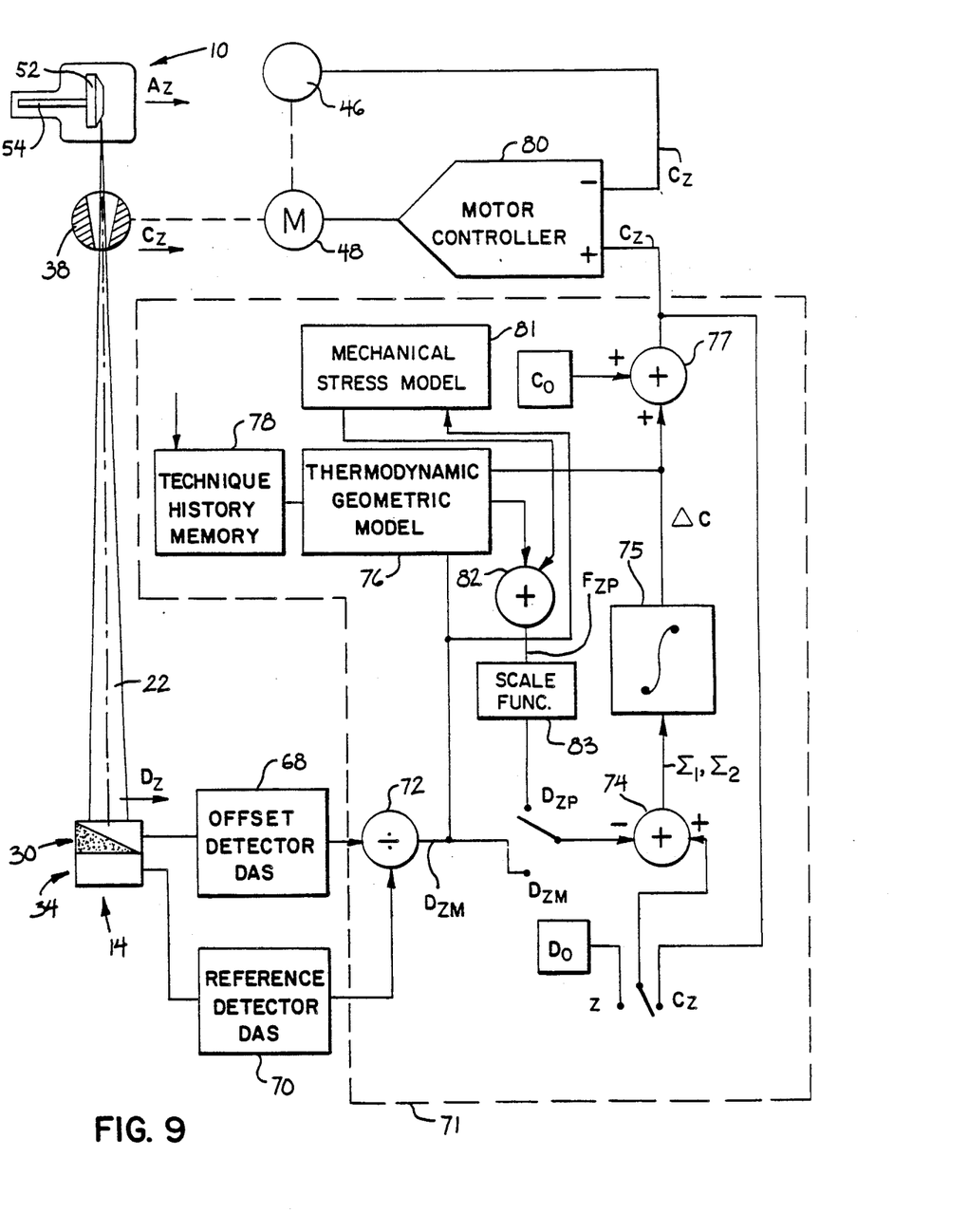
FIG. 9 is a block diagram showing the control system for the collimator of FIG. 3 according to the present invention.

Referring to FIG. 9, a feedback control system controls the position $C_z$ of the collimator 38 in response to changes in the focal spot 26 position $F_z$ for either parallelism correction of z-axis offset correction. The individual elements of the control system may be implemented by a combination of discrete digital and analog functional modules, as are known in the art, or, in the preferred embodiment, by means of a high speed digital computer 71 (not shown) interfaced to analog circuit modules by analog-to-digital and digitally controlled interface circuits to be described. The functional blocks implemented by computer 71 will be indicated in the following discussion by the prefix "software-" and are enclosed in dashed line 71 in FIG. 9.

Signals from the z-axis offset detector 30 and the reference detector 34 are received by an z-axis offset detector data acquisition system ("DAS") 68 and a reference detector DAS 70 for amplification and digitization. The digitized signals are communicated to computer 71.

The signal from the z-axis detector 30, is divided by the signal from the reference detector 34 at software-divider 72, implemented by computer 71 as has previously been described, to produce a fan beam position signal indicating the z-axis position $D_z$ of the exposure area 36 on the detector array 14. Division of these two signals reduces the effect of variations in the intensity of fan beam 22 unrelated to the action of the wedge filter 32. The measured value of $D_z$ produced by the signals from detector array 14 is labeled $D_{zm}$ to distinguish it from the predicted value $D_{zp}$ produced from a software thermodynamic/geometric model and a software mechanical stress model 81 as will now be described.

The previous exposure techniques employed with the x-ray source 10, i.e. x-ray tube voltage, x-ray tube current, and exposure duration, are received from the x-ray source controller (not shown) and stored in computer memory 78 along with the time at which the exposure was initiated, to created a record of the total energy input to the x-ray source 10. A software thermodynamic/geometric model 76 equates the total energy input to the x-ray source 10 as a function of time to the temperature of the various x-ray tube components and thereby predicts the thermal expansion of these tube components and the corresponding movement of the focal spot 26 as a function of time. This software thermodynamic/geometric model 76 may be constructed empirically through observation of a tube of a given design, and recording of the focal spot movements as a function of temperature, time and use. In its simplest implementation the software thermodynamic model 76 incorporates a look-up table holding these measured values.

The technique history stored in memory 78 is used by the thermodynamic/geometric model 76 to produce the predicted value of the focal spot position due to thermal expansion.

Similarly, the software mechanical stress model 81 is a table of empirically determined or analytically computed focal spot movement values as a function of gantry rotation speed and gantry tilt angle. The gantry angle and speed is received by the software mechanical stress model 81 from angular encoders attached to the gantry (not shown) as is understood in the art.

The focal spot movement predicted by the software thermodynamic model 76 is added to the movement predicted by the software mechanical stress model 81 by software adder 82 to provide predicted focal spot position $F_{zp}$. A predicted value of $D_z$, termed $D_{zp}$, is then calculated by software scaler 83 as follows:

$$D_{zp} = -(F_{zp} - \Delta C) \cdot \frac{l_1}{l_2} + \Delta C \qquad (2)$$

where $\Delta C = C_z - C_0$

Referring again to FIG. 9, the negative input of a second software-adder 74 maybe connected either to $D_{zm}$, when the x-ray source 10 is on and $D_{zm}$ may be measured, or to $D_{zp}$ when the x-ray source 10 is off.

One of two error signals $\epsilon_1$ or $\epsilon_2$ is thus produced by the software-adder 74 depending on the type of correction desired. For parallelism correction, $\epsilon_1$ is produced by subtracting $D_z$ from $C_z$:

$$\epsilon_1 = C_z - D_z \qquad (3)$$

A feedback loop controlling the collimator position and described below will act to reduce this error term $\epsilon_1$ thereby making $C_z = D_z$, the condition required for the fan beam plane 62 to be parallel to the imaging plane 60.

For z-axis offset correction, $\epsilon_2$ is produced by subtracting $D_z$ from $D_O$:

$$\epsilon_2 = D_O - D_z \qquad (4)$$

Again the feedback loop controlling the collimator position will act to reduce this error term $\epsilon_2$ thereby making $D_z = D_O$, the condition required for the fan beam exposure area 36 to be aligned with $D_O$.

Error term $\epsilon_1$ or $\epsilon_2$ is integrated as a function of time as indicated by software-integrator 75 to produce a collimator position change signal $\Delta C$ which is summed by means of software-adder 77 to $C_O$ to produce $C_z$, the collimator position. The collimator position $C_z$ is connected to a motor controller 80 to position the collimator 38.

Motor controller 80 is implemented as an analog module distinct from the computer 71 and controlled by a digital signal from the computer 71. The motor controller 80 first converts the Cartesian position $C_z$ to the corresponding polar or rotational coordinates of the collimator actuator and positions the collimator 38 to position $C_z$ by means of feedback loop including motor 48 and position encoder 46. Motor controller 80 also includes a means for offsetting the collimator 38 to the various angular offsets required to bring various of the slots 41 into alignment with the fan beam 21.

During the acquisition of the first projections or after the tube has cooled for a period of time, the error signal $\epsilon_1$ or $\epsilon_2$ is derived from the thermodynamic/geometric model 76, the mechanical stress model 81, and the fan beam position signal $D_{zm}$ from software-divider 72. This procedure is adopted to prevent large amplitude collimator position $C_z$ corrections during the stabilization of $D_{zm}$ upon initial exposure of the z-axis offset detector 30 and reference channel 32.

After the $D_{zm}$ has stabilized, it is reconnected to the software-adder 74 and also serves to correct the predicted value of the fan beam position $D_{zp}$. The value of $D_{zm}$ is also used to correct the value of $F_{zp}$ derived by the thermodynamic model 76 per the following equation:

$$F_{zp} = \Delta C + (\Delta C - D_{zm}) \cdot \frac{l_1}{l_2} \qquad (5)$$

-continued where $\Delta C = C_z - C_0$

The above description has been that of a preferred embodiment of the present invention. It will occur to those who practice the art that many modifications may be made without departing from the spirit and scope of the invention. For example, the fan beam may be aligned to a position that is a compromise between reducing z-axis z-axis offset and reducing parallelism error. In order to apprise the public of the various embodiments that may fall within the scope of the invention, the following claims are made.

I claim:

1. A computed tomography system including an x-ray source for producing a fan beam of x-rays along a fan beam plane in response to an exposure technique, the fan beam plane being at deviation angle $\alpha$ from an imaging plane and intersecting a detector array at position $D_z$, comprising:
   a collimator means having position $C_z$ for controlling the alignment of the fan beam plane;
   a z-axis offset detector positioned to intercept the fan beam for producing a position signal dependant on $D_z$;
   an error calculation means for generating an error signal in response to the position signal; and
   a collimator controller responsive to the error signal for changing the relative position $C_z$ of the collimator with respect to the x-ray source and detector array so as to reduce the magnitude of the error signal.

2. The computed tomography system of claim 1 wherein the error signal is proportional to the difference in position between $D_z$ and an alignment point $D_O$.

3. The computed tomography system of claim 1 wherein the error signal is proportional to the difference between $D_z$ and $C_z$.

4. A computed tomography system including an x-ray source for producing a fan beam of x-rays emanating from a focal at a position $F_z$ spot, along a fan beam plane in response to an exposure technique, the fan beam plane being at deviation angle $\alpha$ from an imaging plane and intersecting a detector array at position $D_z$, comprising:
   a collimator means having position $C_z$ for controlling the alignment of the fan beam plane;
   a memory for storing previous values of exposure techniques used with the x-ray source and the time of each exposure technique;
   a thermodynamic/geometric model for calculating a current fan beam position $D_{zp}$ from the values stored in the memory; and
   a collimator controller responsive to the fan beam position $D_{zp}$ for changing the collimator position $C_z$ in response to $F_z$.

5. The computed tomography system Of claim 4 wherein the collimator controller changes the collimator position so as to reduce the difference between $D_{zp}$ and $C_z$.

6. The computed tomography system of claim 4 wherein the collimator controller changes the collimator position so as to reduce the difference between $D_{zp}$ and the center of the detector array $D_O$.

7. A computed tomography system including an x-ray source, mounted on a gantry for rotation about an axis at a rotational velocity and tilt angle, and for producing a fan beam of x-rays emanating from a focal at a position $F_z$ spot, along a fan beam plane in response to an exposure technique, the fan beam plane being at deviation angle $\alpha$ from an imaging plane and intersecting a detector array at position $D_z$, comprising:
   a collimator means having position $C_z$ for controlling the alignment of the fan beam plane;
   a mechanical stress model for calculating a current fan beam position $D_{zp}$ from the rotational velocity and the tilt angle of the gantry; and
   a collimator controller responsive to the fan beam position $D_{zp}$ for changing the collimator position $C_z$ in response to $F_z$.

8. The computed tomography system of claim 7 wherein the collimator controller changes the collimator position so as to reduce the difference between $D_{zp}$ and $C_z$.

9. The computed tomography system of claim 7 wherein the collimator controller changes the collimator position so as to reduce the difference between $D_{zp}$ and the center of the detector array $D_O$.

* * * * *

UNITED STATES PATENT AND TRADEMARK OFFICE
CERTIFICATE OF CORRECTION

PATENT NO. : 4,991,189

DATED : February 5, 1991

INVENTOR(S) : Boomgaarden, et. al.

It is certified that error appears in the above-identified patent and that said Letters Patent is hereby corrected as shown below:

Col. 9, line 44 "focal at a position Fz spot" should be --focal spot at a position Fz --.

Col. 10, lines 25 and 26 "focal at a position Fz spot" should be --focal spot at a position Fz --.

Signed and Sealed this

Eighteenth Day of August, 1992

Attest:

DOUGLAS B. COMER

*Attesting Officer*    *Acting Commissioner of Patents and Trademarks*